United States Patent
Griffin et al.

(10) Patent No.: US 6,554,787 B1
(45) Date of Patent: *Apr. 29, 2003

(54) HEADBAND FOR TREATMENT OF HEADACHES

(76) Inventors: Brand N. Griffin, Lanier Ford Shaver & Payne, P.C., P.O. Box 2087, Huntsville, AL (US) 35804; Stephen H. Landy, Lanier Ford Shaver & Payne, P.C., P.O. Box 2087, Huntsville, AL (US) 35804

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/385,797

(22) Filed: Aug. 30, 1999

(51) Int. Cl.[7] .............................. A61F 13/00; A61F 7/00
(52) U.S. Cl. ............................... 602/74; 602/2; 602/17; 607/108; 607/109
(58) Field of Search .......................... 602/2, 13, 41–59, 602/60, 61, 62, 63, 64, 65, 74, 75, 78; 607/96, 108–114; 2/311, 312

(56) References Cited

U.S. PATENT DOCUMENTS

| 3,159,160 A | * | 12/1964 | Ullom ........................ 607/109 |
| 4,248,215 A | | 2/1981 | Bleakley et al. |
| 4,326,533 A | | 4/1982 | Henderson |
| 4,382,446 A | | 5/1983 | Truelock et al. |
| 4,676,247 A | * | 6/1987 | Van Cleve ................... 607/112 |
| 4,765,338 A | | 8/1988 | Turner et al. |
| 4,781,193 A | | 11/1988 | Pagden |
| 4,944,289 A | | 7/1990 | Matthews |
| 5,106,004 A | * | 4/1992 | Nguyen ...................... 224/163 |
| 5,314,456 A | | 5/1994 | Cohen |
| 5,400,617 A | * | 3/1995 | Ragonesi et al. ........... 607/109 |
| 5,419,758 A | | 5/1995 | Vijayan |
| 5,529,569 A | | 6/1996 | Woo |
| 5,848,981 A | | 12/1998 | Herbranson |
| 5,920,909 A | * | 7/1999 | Ellsworth et al. .............. 2/171 |

* cited by examiner

Primary Examiner—Kim M. Lewis
(74) Attorney, Agent, or Firm—Lanier Ford Shaver & Payne P.C.; Gerald M. Walsh

(57) ABSTRACT

A headband for the treatment or relief of headaches having a means for attaching said headband to the head thereby producing variable pressure to the head, said headband having one or more pockets for the insertion of treatment elements including cold, heat, vibration, and magnetism; wherein said headband is attached to the head in an annular fashion and headaches are treated or relieved by applying pressure, cold, heat, vibration, or magnetism, or any combination thereof intermittently or continuously.

19 Claims, 3 Drawing Sheets

HEADBAND FOR TREATMENT OF HEADACHES

BACKGROUND OF THE INVENTION

1. Field of the Invention

This invention relates to the therapeutic treatment of pain. In particular, this invention relates to a device for the treatment and relief of headache pain.

2. Description of the Prior Art

Most headaches are generated by brain and surrounding tissues. These headaches can be caused by neuro-vascular, or skeletal muscle abnormalities. Dilation and distention of the extra cranial arteries produce "vascular headaches." Sustained contraction of skeletal muscles of the face, scalp, and neck produce "tension headaches." Headache pain is a very common condition in humans, and a common treatment is the use of oral nonsteroidal anti-inflammatory agents such as aspirin. Other treatment may include muscle relaxants. Such pharmacologic therapy may be ineffective and can be associated with side effects.

Nonpharmacologic treatment in the past has included acupuncture and acupressure as well as message therapy. U.S. Pat. Nos. 4,382,446 and 4,765,338 disclose that the combination of hot and cold applied to the scalp may be beneficial in the treatment of headache. The headband disclosed in these patents can be used to heat or cool but not both simultaneously. U.S. Pat. Nos. 4,248,215, 4,944,289, and 5,419,758 disclose a headband for headache relief using pressure but not heat or cold. U.S. Pat. No. 5,848,981 discloses a headband that uses pressure plus cold for the relief of headaches. U.S. Pat. Nos. 5,314,456 and 4,781,193 disclose headache treatment devices which use both heat and cold but not pressure. In addition, U.S. Pat. No. 5,314,456 further discloses the use of vibration to relieve headache pain and U.S. Pat. No. 5,529,569 further discloses the use of magnetism to relieve headache pain. In general, the prior art suggests that pressure can compress dilated blood vessels, cold can cause dilated blood vessels to constrict, heat can cause contracted muscles to relax, vibration can interfere with the normal sensory transmission of pain, and magnetism may release natural pain-killers.

The present invention makes use of the application of pressure, heat, and cold simultaneously or individually, with or without vibration or magnetism to provide a highly effective, versatile, and practical headband for the treatment or relief of headache pain.

SUMMARY OF THE INVENTION

The present invention is a headband to treat or relieve headache pain, worn around the head above the ears, covering the forehead, the sides of the head and the back of the head. The headband has a belt on a first end and a loop on a second end, and by inserting the belt through the loop a user can cinch or tighten the headband around the head to produce a desired degree of pressure. In one embodiment, the headband is composed of an inner layer and an outer layer forming one or more inner pockets that can be accessed through one or more closeable openings. One or more heating, cooling, magnetic, or vibratory elements can be removably inserted in the inner pocket to provide heat, cold, vibration, magnetism, or a combination thereof to the head and neck. In another embodiment, the headband has an outside surface and an inside surface, with means for removably attaching one or more pockets on the inside surface. A heating, cooling, vibratory, or magnetic element can be inserted into the pocket to provide heat, cold, vibration, magnetism, or a combination thereof to the head and neck by attachment of one or more pockets to the inside surface.

One object of the present invention is to provide a treatment or relief of headache pain.

Another object of the present invention is to provide a headband that is easy to place around the head, is comfortable, and will relieve the pain of headaches.

Another object of the present invention is to provide a headband that fits all head sizes.

Another object of the present invention is to provide a simple, inexpensive headband that can apply pressure, heat, cold, vibration, or magnetism to the head.

A further object of the present invention is to provide continuous treatment or relief of headache pain.

Yet another object of the present invention is to provide pressure, heat, cold, vibration, or magnetism, or any combination thereof simultaneously to the head.

DETAILED DESCRIPTION OF THE PREFERRED EMBODIMENTS

While the following description details the preferred embodiments of the present invention, it is to be understood that the invention is not limited in its application to the details of construction and arrangement of the parts illustrated in the accompanying drawings, since the invention is capable of other embodiments and of being practiced in various ways.

The preferred embodiments of the present invention provide a headband 10 for the treatment or relief of headaches shown in FIGS. 1 through 8.

Figure 1:
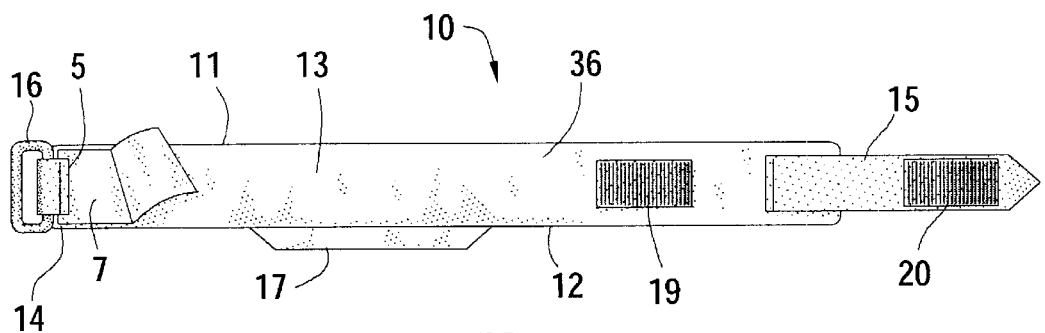
FIG. 1 shows the outer layer and outside surface of the headband.

FIG. 1 shows an embodiment of the headband 10 of the present invention, which has an outer layer 13 and an inner layer 14, viewed from the surface 36 of outer layer 13 which faces away from the head when in use. Headband 10 has a top portion 11 positioned towards the top of the head and a bottom portion 12 positioned towards the bottom of the head when in use. Headband 10 is preferably rectangular in shape but may be fashioned in any suitable shape. Headband 10 is also annular, encircling the head above the ears when in use. A first end of headband 10 has belt-like structure 15 and a second end of headband 10 has a loop or D-ring 16. Belt 15 has a means for attaching belt 15 to headband 10, comprising a hook 19 and pile 20 arrangement.

Figure 2:
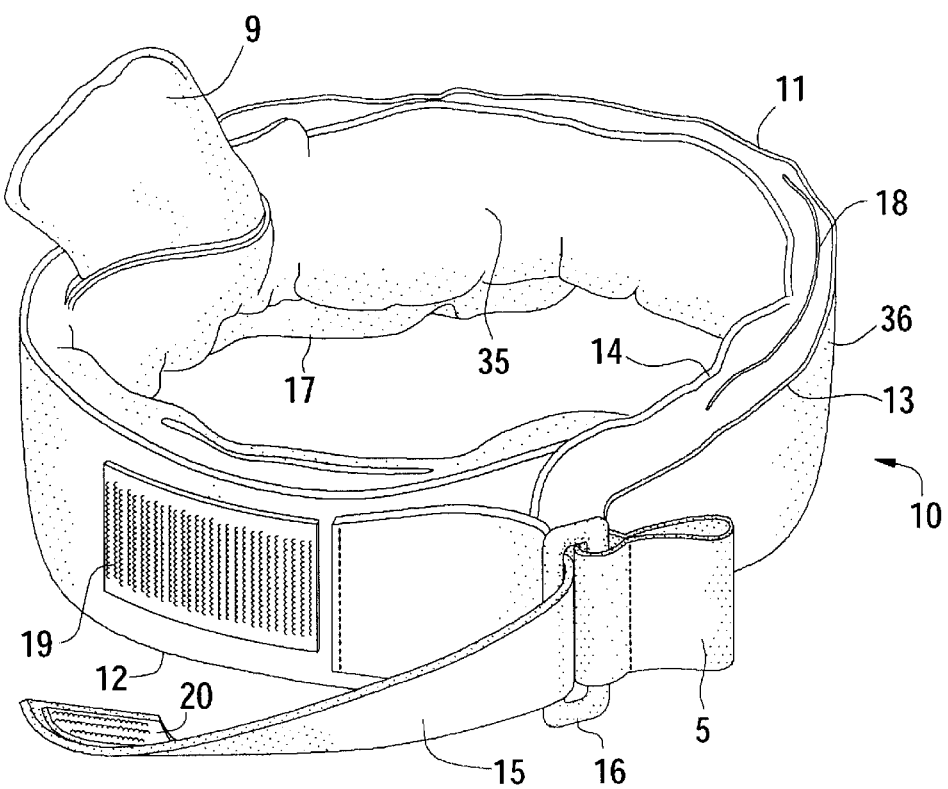
FIG. 2 shows a perspective view of the headband in an annular configuration as when used on the head.

As shown in FIG. 2, when the headband 10 is looped around the head so that the ends are near the forehead, belt 15 is passed through loop 16 and pulled back towards headband 10 to produce desired pressure or tension uniformly around the head. This pressure or tension is maintained when belt 15 is folded over and reversibly attached to the surface 36 of outer layer 13 by hook 19 and pile 20 attachment means. The attachment means are preferably Velcro. The second end of headband 10 also has a pull tab 5 which facilitates pulling belt 15 to create pressure and to complete the attachment of belt 15 to headband 10.

Bottom portion 12 of headband 10 has an elastic strip 17. Elastic strip 17 conforms to the back of the head and applies pressure to the neck region at the back of the head when in use.

Figure 3:
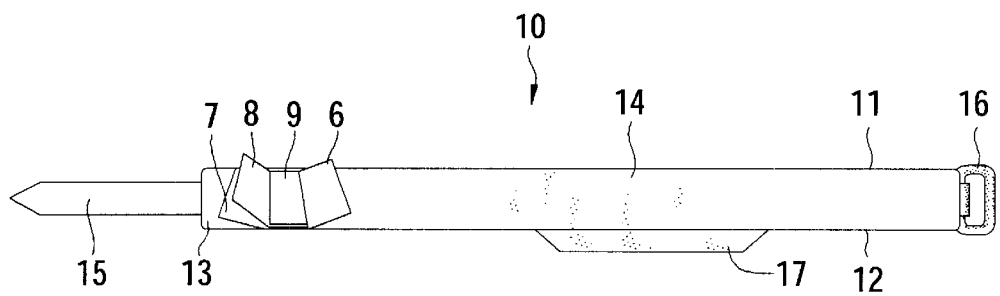
FIG. 3 shows the inner layer of one embodiment of the headband.
Figure 4:
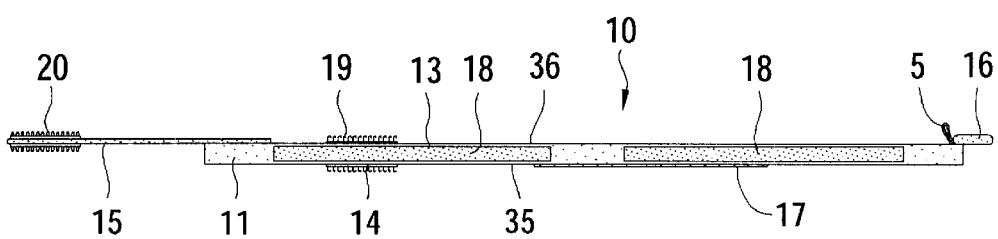
FIG. 4 shows a top view of the headband, showing a closeable opening in the top portion of the headband.
Figure 5:
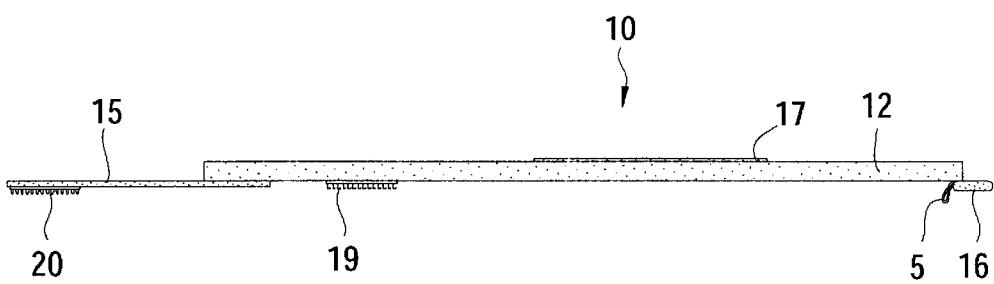
FIG. 5 shows a bottom view of the headband.
Figure 6:
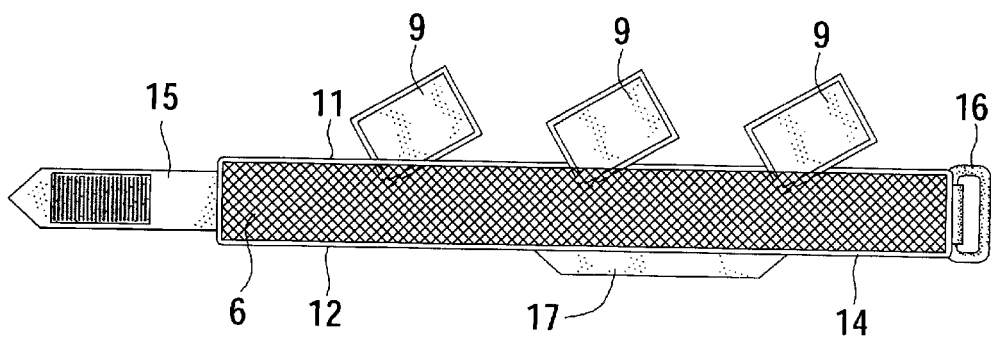
FIG. 6 shows treatment means being inserted into the inner pocket of the headband.

FIG. 3 shows inner layer 14 which faces toward the head when headband 10 is in use. Inner layer 14 is formed in part of a mesh or grid-like structure 6 which defines numerous apertures. Mesh 6 is flexible and cloth-like. Adjacent to outer layer 13 is material for insulation 7 covered with a liner 8. Inner layer 14 is permanently attached to outer layer 13 at the ends of headband 10 and along the entire length of bottom portion 12. Inner layer 14 and outer layer 13 thereby form one or more longitudinal inner pockets with one or more closeable openings 18 FIG. 4 positioned longitudinally along top portion 11. Closeable opening 18 is used to insert one or more various treatment elements 9 for treating or relieving headaches, including, but not limited to, cold, heat, vibration and magnetism. Closeable opening 18 may be reversibly closed by means of one or more zippers or any other suitable means. FIG. 4 shows a top view of belt 10 and top portion 11, showing closeable opening 18. FIG. 5 shows a bottom view of belt 10 and bottom portion 11. FIG. 6 shows treatment elements 9 being inserted into the inner pocket formed by inner layer 14 and outer layer 13.

One or more various treatment elements 9 such as heating, cooling, vibratory, or magnetic elements can be removably placed within the inner pocket through closeable opening 18 and retained therein by closing closeable opening 18. Heating or cooling elements may include appropriate fluidic chemicals that are permanently sealed in plastic malleable pouches or containers, adapted to be refrigerated for cooling or heated for heating. Gel or reusable fluid materials employable in the pouches of packets of the present invention for heat exchange are well known in the art. For example, one reusable, heatable/chillable gel employable in the pouches could be composed of approximately 40% glycerine, 52% distilled water, and 8% starch. It is further well known in the art to provide plastic film pouches, packages, and containers, and heating or refrigerating package constructions of plastic film material. Typical materials making up such films include polyethylene, cellophane, polypropylene, polyester, etc., and laminations thereof. Vibratory treatment elements may include a plastic pouch with material encasing therein a battery operated vibratory motor, with a motor counter weight whose oscillating motion imparts a vibratory motion to the pouch. The degree of vibration may be made variable. Magnetic treatment elements are well known in the art and may include a plastic pouch with material encasing magnets therein. The degree of magnetism may be made variable.

In order to use the headband 10 of the present invention, a gel pack treatment element 9, for example, is rendered cold by placing it in a freezer or hot by placing it in a microwave oven to produce any desired temperature useful for the treatment or relief of headache pain. One or more cold gel packs, hot gel packs, or a combination thereof are placed as treatment elements 9 in the inner pocket of headband 10 and retained therein by reversibly closing closeable opening 18. They can be positioned in any arrangement desired to apply heat or cold to various regions of the head simultaneously. Further, one may substitute one or more vibratory elements or magnetic elements for a gel pack so that one may apply a combination of heat, cold, and vibration or magnetism. Headband 10 is wrapped in an annular fashion around the head above the ears with, preferably, the ends of headband 10 at the front of the head. Belt 15 is passed through loop 16 and headband 10 is tightened around the head by pulling belt 15 towards its origin on headband 10 and folding it over on itself to secure it to attachment means 19 and 20 (See FIG. 2). The more headband 10 is tightened by this means, the more pressure will be exerted to the head by headband 10. A user can create any desired level of pressure to the head by this means. Thus, the headband 10 of the present invention can apply heat, cold, vibration, magnetism or pressure to the head and can also apply any combination thereof simultaneously. For example, one effective application would be to fasten the headband 10 to the head with suitable pressure and apply vibration to the back of the head and heat or cold to the sides of the head. Treatment elements may be replaced continuously without removing the headband so that the headband may be used in the treatment or relief of headache pain continuously.

Mesh 6 forming the inner layer 14 provides a barrier between the heat or cold pouches and the user's head, but allows heat transfer between the pouch and the head because of the net- or grid-like structure of mesh 6. Mesh 6 also facilitates, among other things, the evaporation of moisture.

Figure 7:
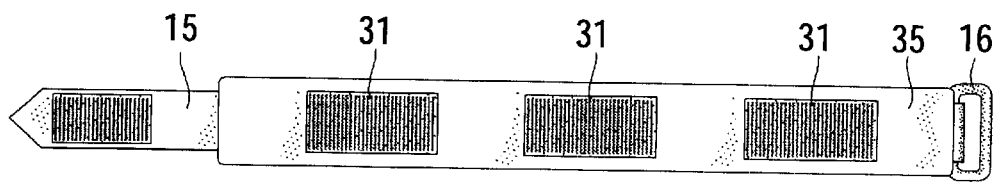
FIG. 7 shows the inside portion of an alternate embodiment of the headband, showing attachment means for removable pockets.
Figure 8:
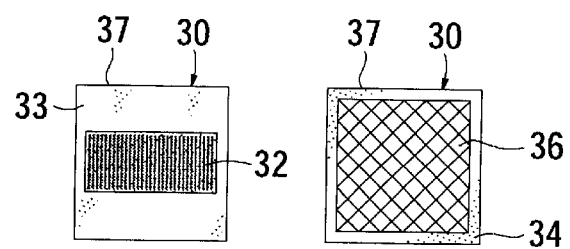
FIG. 8 shows the inside and outside portions of removable pockets, with attachment means on the outside portion and a mesh wall forming the inside portion.

An alternative embodiment of the present invention which does not have an internal pocket or closeable opening 18 is shown in FIGS. 7 and 8. In this embodiment the outer layer 13 and inner layer 14 seen in FIGS. 1–4 form one unit so that headband 10 has an inner surface 35 facing towards the head and an outer surface 36 (see FIG. 4) facing outwards from the head. Belt 15, loop 16, attachment means 19 and 20, pull-tab 5, elastic strip 17, material for insulation 7, and liner 8 are similar to those shown in FIGS. 1–5. The inner surface 35 has a means for attaching one or more detachable pockets 30, said attachment means comprising hook 31. The detachable pocket 30 has an outside portion 33 that contains a means for attachment, said attachment means comprising pile 32, whereby the detachable pocket can be removably attached to inner surface 35 at attachment means 31. Attachment means 31 and 32 are, preferably, Velcro@. Detachable pocket 30 has an inside portion 34 formed, in part, by outer surface 36 which defines numerous apertures. Detachable pocket 30 also has a closeable opening 37 which can be reversibly closed by a zipper or any other suitable means. A treatment means 9 such as a hot, cold, vibrating, or magnetic treatment element is placed in detachable pocket 30 through closeable opening 37 and can be retained therein by reversibly closing closeable opening 37. One or more detachable pockets 30 are then attached to headband 10 on inner surface 35 by attachment means 31 and 32 and headband 10 is used as described previously. This embodiment of the present invention is particularly useful where heat and cold are used simultaneously and it is desirable to isolate and prevent heat exchange between hot and cold pouches.

The foregoing description has been limited to specific embodiments of this invention. It will be apparent, however, that variations and modifications maybe made by those skilled in the art to the disclosed embodiments of the invention, with the attainment of some or all of its advantages and without departing from the spirit and scope of the present invention. For example, the headband and its components may be constructed of plastic, cloth, or leather, or any combination thereof. Attachment means may include various kinds of hooks, snaps, ties, or ligatures, or combinations thereof. The closeable opening may be reversibly closed by hooks, snaps, ties, or Velcro arrangements, or combinations thereof. The treatment elements for heat or cold may be composed of ceramics, metals, or plastics. Material for insulation may be made of various plastic forms or any other suitable insulation materials.

It will be understood that various changes in the details, materials, and arrangements of the parts which have been described and illustrated above in order to explain the nature of this invention may be made by those skilled in the art without departing from the principle and scope of the invention as recited in the following claims.

We claim:

1. A headband, comprising;
   a) a belt and a loop, said belt extending through said loop, wherein said belt is pulled away from said loop by a user to create pressure around the head, said loop providing leverage to adjust said pressure precisely; and
   b) a pull-tab having a first end and a second end, said first end fixed to said loop on an outer surface of said headband, wherein said pull-tab is pulled away from said belt by grasping said second end to facilitate creation of said pressure and to prevent rotation of said headband around the head as the user pulls said belt away from said loop.

2. The headband according to claim 1 wherein said belt has an attachment means for reversibly attaching to said headband to maintain said pressure constant after adjusting said pressure.

3. The headband according to claim 2 further comprising said headband having a first end, a second end, an inner layer, an outer layer, a top portion and a bottom portion, whereby said inner layer and outer layer form a longitudinal inner pocket, said top portion has a closeable opening positioned longitudinally along the top portion to gain access to the inner pocket, said loop and said pull-tab are attached to said first end, and said belt is attached to said second end.

4. The headband according to claim 3 wherein said top portion has a zipper to reversibly close said closeable opening to retain said treatment elements within the inner pocket.

5. The headband according to claim 3 wherein said inner layer is formed, in part, of a mesh which defines numerous apertures, said mesh providing a barrier between the treatment elements and the head and facilitating evaporation of moisture.

6. The headband according to claim 3 wherein said outer layer of the headband has material for insulation, said material being covered with a liner.

7. The headband according to claim 3 further comprising one or more heating, cooling, vibratory, or magnetic treatment elements that are removably inserted in the inner pocket to provide heat, cold, vibration, magnetism, or a combination thereof to the head.

8. The headband according to claim 7 wherein said heating and cooling treatment elements include fluidic chemicals contained within plastic malleable containers suitable for heating or cooling to any degree desired for effective treatment or relief of headache pain.

9. The headband according to claim 8 wherein said fluidic chemicals are composed approximately of 40% glycerine, 52% distilled water and 8% starch.

10. The headband according to claim 3 further comprising an elastic strip on the bottom portion which conforms to the back of the head and applies pressure to the back of the head.

11. The headband according to claim 2 wherein the reversible attachment of the belt to the headband is accomplished by a hook and pile arrangement.

12. A headband, comprising:
   a) a first end having a loop and a pull-tab, said pull-tab having a first end and a second end, said first end fixed to said loop on an outer surface of said headband;
   b) A second end having a belt;
   c) said belt extending through said loop and being pulled back towards said second end to create pressure around the head of a user, said belt using said loop to adjust said pressure precisely;
   d) said pull-tab being pulled away from said second end to facilitate the creation of said pressure and to prevent rotation of said headband around a user's head as said belt is pulled towards said second end; and
   e) an attachment means for reversibly attaching said belt to said headband to maintain said pressure constant after adjusting said pressure.

13. The headband according to claim 12 further comprising said headband having a first end, a second end, an inner layer, an outer layer, a top portion, and a bottom portion, whereby said inner layer and outer layer form a longitudinal inner pocket, said top portion has a closeable opening positioned longitudinally along the top portion to gain access to the inner pocket, said loop and said pull-tab are attached to said first end, and said belt is attached to said second end.

14. The headband according to claim 13 further comprising one or more heating, cooling, vibratory, or magnetic treatment elements that are removably inserted in the inner pocket to provide heat, cold, vibration, magnetism, or a combination thereof to the head.

15. The headband according to claim 13 wherein said top portion has a zipper to reversibly close said closeable opening to retain said treatment elements within the inner pocket.

16. A headband, comprising:
   a) a first end having a loop and a pull-tab, said pull-tab having a first end and a second end, said first end fixed to said loop on an outer surface of said headband;
   b) a second end having a belt;
   c) said belt creating pressure around the head of a user by extending through said loop and being pulled by a user towards said, second end, said loop providing leverage to adjust said pressure precisely;
   d) said pull-tab facilitating the creation of said pressure and preventing said headband from rotating around a user's head by the user pulling said pull-tab away from said second end while pulling said belt towards said second end; and
   e) an attachment means for reversibly attaching said belt to said headband to maintain said pressure constant after adjusting said pressure.

17. The headband according to claim 16 further comprising said headband having a first end, a second end, an inner layer, an outer layer, a top portion, and a bottom portion, whereby said inner layer and outer layer form a longitudinal inner pocket, said top portion has a closeable opening positioned longitudinally along the top portion to gain access to the inner pocket, said loop and said pull-tab are attached to said first end, and said belt is attached to said second end.

18. The headband according to claim 17 further comprising one or more heating, cooling, vibratory, or magnetic treatment elements that are removably inserted in the inner pocket to provide heat, cold, vibration, magnetism, or a combination thereof to the head.

19. The headband according to claim 17, wherein said top portion has a zipper to reversibly close said closeable opening to retain said treatment elements within the inner pocket.

* * * * *